(12) United States Patent
Kuznicki et al.

(10) Patent No.: US 8,017,825 B2
(45) Date of Patent: Sep. 13, 2011

(54) MODIFIED ETS-10 ZEOLITES FOR OLEFIN SEPARATION

(75) Inventors: Steven M. Kuznicki, Edmonton (CA);
Alejandro Anson, Zaragoza (ES);
Tetyana Segin, Edmonton (CA);
Christopher C. H. Lin, Edmonton (CA)

(73) Assignee: The Governors of the University of Alberta, Alberta (CA)

( * ) Notice: Subject to any disclaimer, the term of this patent is extended or adjusted under 35 U.S.C. 154(b) by 351 days.

(21) Appl. No.: 12/316,757

(22) Filed: Dec. 16, 2008

(65) Prior Publication Data
US 2009/0187053 A1 Jul. 23, 2009

(30) Foreign Application Priority Data

Jan. 21, 2008 (CA) .................................... 2618267

(51) Int. Cl.
*C07C 7/13* (2006.01)
(52) U.S. Cl. ..................... 585/829; 585/820; 208/310 Z
(58) Field of Classification Search .................. None
See application file for complete search history.

(56) References Cited

U.S. PATENT DOCUMENTS

| | | | |
|---|---|---|---|
| 3,430,418 A | 3/1969 | Wagner | |
| 4,589,888 A | 5/1986 | Hiscock et al. | |
| 4,717,398 A | 1/1988 | Pearce | |
| 4,853,202 A * | 8/1989 | Kuznicki | 423/326 |
| 4,917,711 A | 4/1990 | Xie et al. | |
| 4,938,939 A | 7/1990 | Kuznicki | |
| 5,011,591 A | 4/1991 | Kuznicki | |
| 5,208,006 A | 5/1993 | Kuznicki et al. | |
| 5,244,650 A | 9/1993 | Kuznicki et al. | |
| 5,365,011 A | 11/1994 | Ramachandran et al. | |
| 5,453,263 A * | 9/1995 | Blosser et al. | 423/713 |
| 5,744,687 A | 4/1998 | Ramachandran et al. | |
| 5,906,954 A | 5/1999 | Koermer | |
| 5,989,316 A | 11/1999 | Kuznicki et al. | |
| 6,068,682 A | 5/2000 | Kuznicki et al. | |
| 6,087,514 A * | 7/2000 | Thangaraj et al. | 549/531 |
| 6,197,092 B1 | 3/2001 | Butwell et al. | |
| 6,200,366 B1 | 3/2001 | Bulow et al. | |
| 6,293,999 B1 | 9/2001 | Cheng et al. | |
| 6,296,688 B1 | 10/2001 | Cheng et al. | |
| 6,387,159 B1 * | 5/2002 | Butwell et al. | 95/99 |
| 6,423,881 B1 | 7/2002 | Yang et al. | |
| 6,497,750 B2 | 12/2002 | Butwell et al. | |
| 6,517,611 B1 | 2/2003 | Kuznicki et al. | |
| 6,867,166 B2 | 3/2005 | Yang et al. | |

OTHER PUBLICATIONS

Kotelnikov, et al, Application of FBD process for C3-C4 olefins production from light paraffins, Stud. Surf. Sci. Catal., 2004, pp. 67-72, v147.
Paul F. Bryan, Removal of Propylene fron Fuel-Grade Propane, Sep. Purif. Rev., 2004, pp. 157-182, vol. 33, No. 2.
Kirk-Othmer Encyclopedia of Chemical Technology, Adsorption, Gas Separation, 2001, vol. 1, pp. 617-647, John Whiley & Sons, Inc., Online Edition.
Choudary, et al, Adsorption of Light Hydrocarbon Gases on Alkene-Selective Adsorbent, Ind. Eng. Chem. Res., 2002, 41, 2728-2734.
Miltemburg, et al, Adsorption of Light Olefin/Paraffin Mixtures, Chem. Eng. Res. and Des. May 2006, 84(A5), pp. 350-354.
Al-Baghli, et al, Binary and Ternary Adsorption of Methane, Ethane, and Ethylene on Titanosilicate ETS-10 Zeolite, J. Chem. Eng. Data, 2006, 51, 248-254.
Al-Baghli, et al, Adsorption of Methane, Ethane, and Ethylene on Titanosilicate EST-10 Zeolite, J. Chem. Eng. Data. 2005, 50, 843-848.
Rouquerol, et al, Adsorption by Powders and Porous Solids, 1999, pp. 1-26 and 165-189, Academic Press, San Diego, California.
Myers, et al, Thermodynamics of Mixed-Gas Adsorption, 1965, pp. 121-127, A.I.Ch.E. Journal, vol. 11, No. 1.
Valenzuela, et al, "Caluclations fo Mixed-Gas Adsorption from Single-Gas Isotherms", Adsorption Equilibrium Data Handbook, 1989, pp. 208-217, Prentice Hall, Englewood, N.J.
Greg, et al, "The Use of Gas Adsorption for the Determination of Surface Area and Pore Size Distribution", Adsoprtion, Surface Area and Porosity, 1982, pp. 283-286, Academic Press, London-New York.

* cited by examiner

*Primary Examiner* — Tam M Nguyen
(74) *Attorney, Agent, or Firm* — Kenneth H Johnson

(57) ABSTRACT

An as prepared Na-ETS-10 zeolite was modified by ion exchange with a mono-, di-, or tri-valent cation and mixtures thereof. Several of the modified ETS-10 zeolites showed improved pressure swing capacity during the selective adsorption of ethylene from an ethylene/ethane mixture, relative to Na-ETS-10, although the selectivity of adsorption decreased. Modification with $Ba^{2+}$ and $Ba^{2+}/H^+$ provided modified ETS-10 zeolite adsorbents having a good balance of selectivity and pressure swing capacity for the separation of ethylene/ethane mixtures, making them useful adsorbents for PSA processes.

18 Claims, 6 Drawing Sheets

Figure 1a
(Unmodified)

Figure 1b
(K modified)

**Figure 1c
(Li modified)**

**Figure 1d
(Ba modified)**

Figure 1e
(Ba/H modified)

Figure 1f
(La/H modified)

Figure 1g
(Ag modified)

Figure 1h
(Cu modified)

MODIFIED ETS-10 ZEOLITES FOR OLEFIN SEPARATION

FIELD OF THE INVENTION

The present invention relates to the adsorptive separation of olefins from paraffins. Specifically, a cation modified, large pore titanosilicate having a good pressure swing capacity, is used to selectively adsorb ethylene form a mixture of ethylene and ethane at ambient temperatures.

BACKGROUND OF THE INVENTION

The commercial production of olefins such as ethylene and propylene relies mainly on the pyrolysis of light hydrocarbon feeds at high temperatures. Thermal cracking of ethane, propane or higher hydrocarbons invariably leaves un-cracked paraffins and other undesirable compounds in the product stream. The undesirable paraffins (e.g. ethane, propane etc.) must be separated from ethylene, propylene and other products which, due to the similar boiling points of paraffins and olefins having the same carbon number, requires the use of energy intensive cryogenic distillation columns. Such "super-fractionations" represent a significant portion of the cost associated with running a cracking unit. Specifically, it would be beneficial if expensive C2 or C3 splitter columns could be augmented or replaced.

In the interests of reducing cost and operating complexity, several methods have been explored to replace the expensive separation processes used in traditional hydrocracking plants. These include selectively adsorptive membranes (see for example U.S. Pat. Nos. 6,395,067; 6,340,433; Kotelnikov et al. in *Stud. Surf. Sci. Catal.* 2004, v 147, p 67 and Bryan et al. in *Sep. Purif. Rev.* 2004, v 33, p 157), liquid extraction systems, and pressure swing adsorption methods (see for example U.S. Pat. Nos 3,430,418; 4,589,888; and 6,497,750).

Pressure swing adsorption (PSA) processes generally include i) a high pressure adsorption step, during which a component in a gaseous mixture is selectively adsorbed onto an adsorbent substrate ii) a purging step, during which non-adsorbed components are collected as waste, recycle or product effluent; and iii) a low pressure de-sorption step or regeneration step, during which the selectively adsorbed component is released form the adsorbent substrate (see for example, U.S. Pat. No. 6,197,092 that is incorporated herein by reference). In a PSA processes, the adsorbent material is typically packed in one or more beds, and various pressurization/depressurization protocols including the application of vacuum can be used (see Adsorption, Gas Separation in the Kirk-Othmer Encyclopedia of Chemical Technology, Copyright John Wiley & Sons, Inc. vol 1, pg 617 and references cited therein).

Several types of adsorbents have been developed for the separation of various gas mixtures by PSA processes, and the useful application of each depends mainly of the nature of the gases to be separated. PSA, and similar separation processes such as thermal swing adsorption (TSA), may utilize a kinetically effected separation, which excludes one potential adsorbent due to pore diameter restrictions in the adsorbent, and/or thermodynamically effected separation, in which one potential adsorbate binds more strongly to the adsorbent than another potential adsorbate under equilibrium conditions. Thermodynamic separations may be facilitated by electrostatic or bonding interactions between an adsorbent material and an adsorbate molecule.

Adsorbents for the separation of olefins from paraffins often include high surface area, porous materials which have been treated with metal species capable of $\pi$-complexation with olefins, such as copper and silver salts. For example, U.S. Pat. No. 4,917,711 describes the use of supports such as zeolite 4A, zeolite X, zeolite Y, alumina and silica, each treated with a copper salt, to selectively remove carbon monoxide and/or olefins from a gaseous mixture containing saturated hydrocarbons (i.e. paraffins) such as ethane and propane.

U.S. Pat. Nos 6,867,166 and 6,423,881 describe the use of copper salts and silver compounds supported alternatively on silica, alumina, MCM-41 zeolite, 4A zeolite, carbon molecular sieves, polymers such as Amerberlyst-35 resin, and alumina to selectively adsorb olefins from gaseous mixtures containing olefins and paraffins. Both kinetic and thermodynamic separation behavior was observed and modeled.

Clay based adsorbents which have been treated with silver salts are taught by Choudary et al. in the *Ind. Eng. Chem. Res.* 2002, v 41, p 2728. The article describes $Ag^+$ impregnated clay adsorbents that are selective for olefin uptake from a gaseous olefin/paraffin mixture. Up to 20% of the olefin is adsorbed in an irreversible manner. The adsorbent was evaluated for its performance in a four bed vacuum swing adsorption process. Ethylene was separated from ethane with over 85% recovery and in over 99% purity.

An article in *Chemical Engineering Research and Design*, 2006, 84(A5) p 350, by Van Miltenburg et al. reported the use of $Cu^+$ to modify Faujasite zeolites. The modified zeolites were useful adsorbents for the separation of ethylene from ethylene/ethane mixtures. The use of similarly modified Faujasite zeolites in a highly selective PSA process that separates carbon monoxide and/or olefins from a mixture that also contained paraffins was reported in U.S. Pat. No. 4,717,398 assigned to BP.

In U.S. Pat. Nos 5,744,687; 6,200,366 and 5,365,011 assigned to BOC, copper modified 4A zeolites were used to separate ethylene and propylene form ethane and propane respectively. Elevated temperatures were required for successful application to PSA processes (i.e. from 50° C. to 200° C.). Zeolites such as zeolite 5A and zeolite 13X were also used in the formation of copper modified adsorbents.

U.S. Pat. No. 6,293,999 assigned to UOP, describes the use of aluminophosphates to separate propylene from propane in a PSA process. The aluminophosphate is a small pore molecular sieve designated "AlPO-14". The system operates at temperatures of from 25° C. to 125° C. to effect a kinetic separation of propylene from propane. U.S. Pat. No. 6,296,688 also to UOP, discloses a vacuum swing adsorption process for separating propylene form propylene/propane mixtures using analogous zeolite adsorbents.

Despite the above progress, new materials having high selectively and good pressure swing capacity are still needed for olefin/paraffin separation processes. Particularly desirable are adsorbents that can be tuned to suit commercial process conditions or adsorbents that are effective in ambient temperature PSA separation of olefin/paraffin mixtures.

In U.S. Pat. Nos 4,938,939 and 5,011,591, assigned to Engelhard Corp., a new family of crystalline titanium silicate zeolite materials was disclosed.

U.S. Pat. No. 4,938,939, describes a small pore zeolite, designated "ETS-4" with pore diameters of about 3-5 Å. Modification of the ETS-4 materials by cation exchange with for example, $Ba^{2+}$ and $Sr^{3+}$ gave adsorbents which were useful in the separation of nitrogen from methane using PSA processes (see U.S. Pat. Nos 6,068,682 and 5,989,316).

As described in U.S. Pat. No. 6,517,611, heat treatment of ETS-4 gave a controlled pore volume zeolite material, dubbed "CTS-1" which is a highly selective absorbent for olefin/paraffin separations. The CTS-1 zeolite, which has pore diameters of from about 3-4 Å, selectively adsorbed ethylene from a mixture of ethylene and ethane through a size exclusion process. The pore diameter of CTS-1, allowed diffusion of ethylene, while blocking diffusion of ethane which was too large to enter the pores of the CTS-1 zeolite, thereby providing a kinetic separation. The CTS-1 adsorbent was successfully applied to a PSA process in which ethylene or propylene could be separated from ethane or propane respectively.

U.S. Pat. No. 5,011,591 discloses the synthesis of a large pore diameter titanosilicate designated "ETS-10". In contrast to ETS-4 and CTS-1, the large pore titanosilicate material, ETS-10, which has pore diameters of about 8 Å, cannot kinetically distinguish light olefins from paraffins of the same carbon number. Nevertheless, high degrees of selectivity have been reported for the separation of ethylene from ethane using as prepared ETS-10 zeolites; see: Al-Baghli and Loughlin in *J. Chem. Eng. Data* 2006, v 51, p 248. The authors demonstrate that Na-ETS-10 is capable of selectively adsorbing ethylene from a mixture of ethylene and ethane under thermodynamic conditions, even at ambient temperature. Although, the reported selectivity for ethylene adsorption using Na-ETS-10 was high at ambient temperature, the adsorption isotherms for ethylene and ethane had highly rectangular shapes consistent with a low pressure swing capacity. Consequently, Na-ETS-10 is not readily applicable to pressure swing absorption processes (PSA), at least at lower or ambient temperatures.

We have now found that the separation selectivity and pressure swing capacity of Na-ETS-10 can be dramatically affected by cation exchange. The resulting modified ETS-10 zeolites provide more useful pressure swing capacities for olefin/paraffin separation. In addition, the modified ETS-10 zeolites can be precisely tuned by cationic exchange to cover a range of adsorbent behavior from silica type adsorbents (i.e. weak adsorbents) to more traditional zeolites (i.e. strong adsorbents). Hence, the ETS-10 zeolites can be modified to suit a wide range of PSA process conditions for the separation of olefins from paraffins and in some cases are suitable for ambient temperature PSA.

SUMMARY OF THE INVENTION

Provided is a method for the selective sequestration of ethylene from a gaseous mixture comprising ethylene and ethane, wherein said method comprises: passing said mixture over an adsorbent which selectively adsorbs ethylene from said mixture, said adsorbent comprising a modified ETS-10 zeolite.

The present invention provides a method of increasing the proportion of olefin in a gaseous mixture comprising said olefin and a paraffin having the same number of carbon atoms as said olefin, wherein said process comprises: (a) passing said mixture over a modified ETS-10 zeolite at a temperature and pressure wherein said modified ETS-10 material selectively adsorbs said olefin from said mixture, and (b) lowering the pressure and optionally increasing the temperature to release the selectively adsorbed olefin from said modified ETS-10 zeolite.

The invention improves the applicability of large pore titanosilicate zeolites to PSA processes which separate olefins and paraffins of the same carbon number by increasing the pressure swing capacity of the zeolites though cation exchange modification.

The present invention also teaches the use of structural variants of unmodified ETS-10 as adsorbents for the selective uptake of olefins from a gaseous mixture of olefins and paraffins having the same number of carbon atoms.

The current invention provides a cationically modified ETS-10 zeolite having a superior pressure swing capacity relative to unmodified ETS-10 for the separation of olefins and paraffins having the same number of carbon atoms.

The current invention provides a cationically modified ETS-10 zeolite having a superior pressure swing capacity in the pressure range of about 1 kPa to about 200 kPa, relative to unmodified ETS-10 for the separation of olefins and paraffins having the same number of carbon atoms.

In an aspect of the invention, a cationically modified ETS-10 zeolite with attenuated selectivity but with improved pressure swing capacity for application to the separation of ethylene from ethane in pressure cycling processes, is provided.

In an aspect of the invention, as prepared Na-ETS-10 is modified by a mono-, di, or tri-valent cation to provide a modified ETS-10 which selectively absorbs olefins from a mixture of olefins and paraffins having the same number of carbon atoms.

In another aspect of the invention, cationic modification of as prepared Na-ETS-10 provides an adsorbent for the PSA separation of olefins and paraffins having the same number of carbon atoms, at ambient temperatures.

The current invention provides a method to adjust the adsorption selectivity and the pressure swing capacity of an as prepared Na-ETS-10 zeolite for use in a pressure swing adsorption (PSA) separation of ethylene and ethane, said method comprising: modifying said as prepared Na-ETS-10 zeolite by cation exchange with one or more than one mono-, di- or tri-valent cation or mixtures thereof.

A pressure swing adsorption process is provided for increasing the proportion of an olefin in a gaseous mixture comprising said olefin and a paraffin having the same number of carbon atoms as said olefin, wherein said process comprises: (a) passing said mixture through a bed comprising a modified ETS-10 zeolite at a pressure at which the bed selectively adsorbs said olefin to give a waste or recycle stream enriched in paraffin; (b) reducing the pressure in said bed to a pressure at which the bed releases said adsorbed olefin to give a product stream enriched in olefin; wherein said modified ETS-10 zeolite comprises an as prepared Na-ETS-10 zeolite which has been modified by cation exchange with one or more than one mono-, di- or tri-valent cation or mixtures thereof.

In an aspect of the current invention, the molecular sieve "ETS-10" is modified to control its selectivity towards ethane and ethylene binding for the partial separation of the same under desired process conditions. The modified ETS-10 zeolites can be used in PSA adsorption processes which when combined with cryogenic distillation, can reduce the energy requirements and manufacturing costs in the manufacture of ethylene from ethane by a thermal hydrocracking processes.

A process is provided for the selective removal of ethylene from a gaseous mixture comprising ethylene and ethane, said gaseous mixture being a product feedstream from an ethane hydrocracking unit, wherein said process comprises: passing said mixture over an adsorbent which selectively adsorbs ethylene from said mixture, said adsorbent comprising an as prepared Na-ETS-10 zeolite which has been modified by cation exchange with one or more than one mono-, di- or tri-valent cation or mixtures thereof.

A process is provided for the separation of an olefin from a mixture comprising said olefin and a paraffin having the same number of carbon atoms as said olefin, wherein said mixture is subjected to both cryogenic distillation and pressure swing adsorption (PSA), said PSA comprising: (a) passing said mixture through one or more PSA units containing a modified ETS-10 zeolite which selectively adsorbs said olefin, and (b) regenerating said one or more PSA units to produce a product stream enriched in said olefin.

In another embodiment of the invention, one or more PSA units containing a modified ETS-10 zeolite increase the ethylene concentration in a C2 product stream immediately upstream or immediately downstream of a C2 splitter column; said C2 splitter column receiving the C2 product stream in a hydrocarbons cracking plant.

DETAILED DESCRIPTION OF PREFERRED EMBODIMENTS

The present invention relates to the use of adsorbents comprising modified titanium silicate molecular sieves for the separation of olefins from a mixture of olefins and paraffins having the same number of carbon atoms.

As used herein the term "olefin" refers to α-olefins or "alpha" olefins and connotes a terminal olefin or a 1-olefin, in which the double bond resides only at the terminal position (as opposed to an internal olefin, in which the double bond is at an internal site). Some specific olefins include but are not limited to ethylene, propylene, and 1-butene. The term "paraffin" refers to any fully saturated hydrocarbons and includes but is not limited to ethane, propane, n-butane, n-pentane and the like. In the current invention the olefins and paraffins are preferably gaseous under the process conditions and have from 2 to 6 carbon atoms, with ethane and ethylene being the most preferred olefin and paraffin respectively.

As used herein, the term "modified" encompasses cationic modification and structural modification (or structural variation) of an as prepared ETS-10 zeolite.

As used herein the term "cationic modifier" represents a cation, typically delivered in the form of a salt or acid, which when added to an unmodified ETS-10 zeolite, provides a modified ETS-10 zeolite through cation exchange reactions.

As used herein the term "structural modifier" represents a compound, which when added to an unmodified ETS-10 zeolite, provides a modified ETS-10 zeolite through substitutions of Ti and/or Si sites or through extraction of a portion of the titanium present. Structural modifiers can also be added during the synthesis of an unmodified ETS-10 to give instead a modified ETS-10 zeolite.

As used herein, the term "pore diameter" refers to the effective diameter of the largest gas molecules that are significantly adsorbed by the ETS-10 zeolite materials. This may be similar to, but different from the crystallographically determined pore diameter of the ETS-10 zeolite material.

As used herein the terms "separate" or "separation" as well as "selective removal" connote a partial or full separation of at least one component in a gaseous mixture. Hence at least one component may be completely removed or isolated (i.e. purity of 90% or higher) or merely enriched (i.e. the concentration or proportion of a component in a gaseous mixture is increased beyond its initial value) during the process of the current invention.

As used herein the term "pressure swing capacity" has its conventional meaning and generally refers to the amount (in millimoles per gram, mmol/g) of gaseous component (i.e. an olefin or a paraffin) that can be adsorbed on and desorbed from an adsorbent, between a first higher pressure and a second lower pressure respectively. In the current invention, the pressure swing capacity is reported as the amount of a gaseous component that can be absorbed and/or desorbed over a given pressure range at a given temperature as indicated by an adsorption isotherm. It will be obvious to a person skilled in the art, that a "swing capacity" for a temperature range can be similarly defined.

Unmodified or "as prepared" ETS-10 zeolites which are herein designated "Na-ETS-10" zeolites, mainly contain $Na^+$ as exchangeable counterions but in some cases, depending on preparation conditions, may also contain exchangeable $K^+$ counterions. The unmodified titanium silicate molecular sieves (i.e. Na-ETS-10) of the current invention have octahedral titanium sites and tetrahedral silicon sites, providing a structure with an average pore diameter of approximately 8 Å and a titania/silica mol ratio of from 2.5 to 25. A non-limiting description of unmodified ETS-10 zeolites is given in Table 1 of *J. Chem. Eng. Data.* 2005, 50, p 843 by Al-Baghli et al. that is incorporated herein by reference.

The "modified" ETS-10, titanium silicates are derived from "as prepared" or unmodified ETS-10 zeolites through cation exchange reactions and/or structural exchange reactions. Alternatively, modified ETS-10 zeolites may be obtained by manipulation of the preparative recipe and conditions used for making Na-ETS-10. All such modifications are contemplated by the current invention, provided that the modified ETS-10 zeolite remains selective for the adsorption of olefins over paraffins.

In the current invention, the terms "modified" or "modified ETS-10 zeolite" connote an Na-ETS-10 zeolite in which at least some of the exchangeable $Na^+$ and/or $K^+$ ions originally present in the zeolite are replaced by other cationic species by cationic exchange reactions. Such modifications are "cationic modification(s)". The terms "modified" or "modified ETS-10 zeolite" also connote a titanium silicate zeolite which differs from an as prepared Na-ETS-10 zeolite by one or more substitutions at the octahedral titanium sites or the tetrahedral silicon sites (i.e. a structural variant of Na-ETS-10 in which a partial exchange of Ti and/or Si has occurred). Such Ti and/or Si substitutions are structural in nature and for the purposes of the current invention are designated "structural modification(s)". Hence, in the current invention, the terms "modified" or "modified ETS-10 zeolites" includes ETS-10 zeolites that have either or both of:

i) substitution of exchangeable cations (e.g. $Na^+$ and/or $K^+$ sites);

ii) substitution at the titanium and/or silicon sites.

By way of non-limiting example, an Na-ETS-10 can be cationically modified by stirring the Na-ETS-10 zeolite with a suitable 3ation source, to exchange some of the exchangeable cations originally present in the Na-ETS-10.

Structural variations to the Ti or Si sites of Na-ETS-10 can be achieved by modifying or changing the source components used to make the Na-ETS-10. Structural modification can also be achieved though use of exchange reactions where the Ti and/or Si sites of "as prepared" Na-ETS-10 are substituted by suitable metal species, after the Na-ETS-10 material is isolated. Both types of structural modification are known in the art and are discussed in U.S. Pat. Nos. 5,244,650 and 5,208,006.

Members of the ETS-10 molecular sieve zeolite type, have a crystalline structure and an X-ray powder diffraction pattern with significant lines at or near those disclosed in Table 1 of U.S. Pat. No. 5,011,591 the entirety of which is incorporated herein by reference. By "near" it is meant that the major lines can shift, on modification of Na-ETS-10, by as much as 1 unit or more, but will maintain essentially the same pattern in an X-ray powder diffraction pattern. Hence, modified ETS-10 zeolites will have the substantially the same pattern of major lines in an X-ray powder diffraction pattern as unmodified Na-ETS-10.

As prepared ETS-10 zeolites can be prepared by mixing a source of silica (e.g. silica; silica hydrosol; silica gel; silicic acid; alkoxides of silicon; alkali metal silicates such as but not limited to sodium and potassium silicate; mixtures thereof and the like); a source of trivalent titanium (e.g. $TiCl_3$ etc.); a base such as but not limited to an alkali metal hydroxide (e.g. NaOH, NaOH(aq), KOH, etc.) for controlling the pH of the reaction mixture at from 9.9 to 10.3±0.1; water; and optionally an alkali metal halide (NaCl, NaF, KF etc.) in specific ratios. In an aspect of the invention, Na-ETS-10 is prepared from a reaction mixture having a composition in terms of mole ratios of:

$SiO_2/Ti$=from about 2 to about 20
$H_2O/SiO_2$=from about 2 to about 100
$M_n/SiO_2$=from about 0.1 to about 10

For further suitable, but non-limiting ratios of these source components see Table 2 of U.S. Pat. No. 5,011,591 that is incorporated herein by reference. The mixture is typically heated to a temperature of between 100° C. and 200° C. and stirred for at least 8 hours. The "as prepared" Na-ETS-10 zeolite forms as crystals within the reaction mixture. Stirring of the reaction mixture is beneficial but in some cases is optional, especially when using silica gel as the source of silica. The crystals are separated by filtration and optionally washed with water, followed by drying at temperatures of up to about 250° C. for up to about 72 hours.

In an aspect of the invention, the "as prepared" or unmodified Na-ETS-10 is a zeolite prepared according to Examples 5, 6, 7 or 9 of U.S. Pat. No. 5,011,591.

In an aspect of the invention, unmodified Na-ETS-10 zeolite is prepared and isolated prior to modification by cation exchange reactions or structural substitution reactions.

Both "as prepared" and "cationically modified" ETS-10 zeolites have a composition that in some aspects of the invention may be represented by the following formula:

x $M_{2/n}O:TiO_2$:y $SiO_2$:z $H_2O$, where M is a mono-, di-, or tri-cationic ion, n is the valence of M, x is from 1 to 10, y is from 2.5 to 25, and z is from 0 to 150. In "as prepared" or unmodified titanium silicate, M is sodium and/or potassium. In cationically modified ETS-10, sodium and/or potassium ions are ion exchanged for at least one cation not originally present in the "as prepared" or unmodified titanium silicate. Alternatively, in cationically modified ETS-10 zeolites, the $Na^+$ ions can be replaced with $K^+$ ions.

The cation exchange capacity (CEC) is a measure of the exchangeable cations present in an ETS-10 zeolite. It can be measured in SI units as the positive charge (in coulombs) absorbed by the zeolite per unit of mass of the zeolite. It is also conveniently measured in milliequivalents per gram of zeolite (meq/g) or per 100 gram of zeolite (meq/100 g). The cation exchange capacity of the unmodified zeolites is not specifically defined, but in one aspect of the invention the CEC can be at least 50 millequivalents per 100 g. In another aspect of the invention, the unmodified zeolite can have a CEC of from about 1.0 to about 10 meq/g.

The percentage of ions exchanged during the formation of the cationically modified ETS-10 zeolite is not specifically defined, provided that the adsorbent remains selective for the adsorption of olefins over paraffins. By way of a non-limiting example, from about 5% to 100% of the exchangeable $Na^+$ and/or $K^+$ ions originally present in the "as prepared" ETS-10 may be exchanged by cation exchange.

In an aspect of the invention, the amount of cation added to the unmodified ETS-10 can be from about 1% to about 1000% of the cationic exchange capacity of the zeolite, preferably from about 25% to about 250%. One or more than one type of cationic modifier can be added to Na-ETS-10. For example, a first cationic modifier may be added by treating an as prepared Na-ETS-10 zeolite with a cation in concentrations (meq/g) below the CEC of the zeolite, followed by the addition of a second, third, or fourth etc. cationic modifier to replace some or all of the remaining exchangeable $Na^+$ and $K^+$ sites. Cationic exchange can involve sequential or simultaneous addition of one or more of the same or different cationic modifiers to an unmodified ETS-10 zeolite.

In the current invention, modification can include partial or full replacement of exchangeable $Na^+$ and/or $K^+$ ions for one or more than one mono, di- or tri-valent cation or mixture thereof. Modification can also include partial or complete replacement of exchangeable $Na^+$ ions for $K^+$ ions.

In an aspect of the invention, the modified ETS-10 zeolite is an "as prepared" ETS-10 zeolite that has been cation exchanged with a mono, di- or tri-valent cation or mixture thereof. Either or both of $Na^+$ or $K^+$ may be ion exchanged for a mono-, di- or tri-valent cation.

In an aspect of the invention, the mono-, di- and tri-valent cations are selected from the group 2-4 metals, a proton, ammonium compounds and mixtures thereof. Some specific non-limiting examples of mono-, di, or tri-valent cations that can be used in the current invention include, $Li^+$, $K^+$, $Cs^+$, $Mg^{2+}$, $Ca^{2+}$, $Sr^{2+}$, $Ba^{2+}$, $Sc^{3+}$, $Y^{3+}$, $La^{3+}$, $Cu^+$, $Cu^{2+}Zn^{2+}$, $Cd^{2+}$, $Ag^+$, $Au^+$, $H^+$, $NH_4^+$, and $NR_4^+$ where R is an alkyl, aryl, alkylaryl, or arylalkyl group.

The cationic modifiers are generally added to unmodified Na-ETS-10 in the form of a salt or an acid. The anionic counterion associated with the cationic modifier is not specifically defined, provided that is does not adversely affect the modification (i.e. cation exchange) reactions. Suitable anions include but are not limited to acetate, carboxylate, benzoate, bromate, chlorate, perchlorate, chorite, citrate, nitrate, nitrite, sulfates, and halide (F, Cl, Br, I) and mixtures thereof. Suitable acids include inorganic and organic acids, with inorganic acids being preferred.

The Na-ETS-10 zeolite may be cation exchanged by any of the known conventional techniques. For example, a Na-ETS-10 zeolite may be cation exchanged by treatment with a cationic modifier in a stirred aqueous solution. After the cation exchange reactions are carried out, the resulting modified ETS-10 zeolites can be treated in any conventional manner, including but not limiting to washing and drying steps as well as calcinations and granulation steps.

In an aspect of the invention, the modified ETS-10 zeolite is an "as prepared" ETS-10 zeolite that has been structurally modified. Either or both of Ti and Si may be substituted by an octahedral metal and tetrahedral metal respectively.

In an aspect of the invention, titanium is partially substituted by an octahedral metal selected from the group consisting of but not limited to arsenic, cobalt, chromium, copper, iron, germanium, hafnium, magnesium, manganese, molybdenum, niobium, nickel, antimony, tin, uranium, vanadium, yttrium, zinc, zirconium, lanthanum, an actinide a lanthanide and mixtures thereof.

In an aspect of the invention, silicon is partially substituted by a tetrahedral metal selected from the group consisting of but not limited to aluminum, arsenic, bismuth, boron, beryllium, cobalt, chromium, copper, iron, gallium, germanium, indium, lead, magnesium, manganese, molybdenum, niobium, nickel, antimony, tin, titanium, vanadium, tungsten, zinc and mixtures thereof.

Structurally modified ETS-10 zeolites have a composition that in some aspects of the invention may be represented by the following formula:

$$a(1.0 \pm 0.25)M_{2/n}O:AO_\alpha:d\ BO_\beta:0\text{-}100\ H_2O,$$

where M is at least one cation of valence n; $\alpha$ is ½ the valence of A; $\beta$ is ½ the valence of B; d is 2-100; a is equal to ½ the charge provided by the total of A and B; A is octahedrally coordinated titanium alone or a mixture of octahedrally coordinated titanium and another octahedrally coordinated metal; B is silicon alone or a mixture of silicon and another tetrahedrally coordinated metal; provided that when A is only titanium, B cannot be only silicon and that when B is only Si, A cannot be only Ti.

In an aspect of the invention, structurally modified ETS-10 zeolites are crystalline molecular sieves having a pore size of at least 8 Angstrom units.

In an aspect of the invention, A is titanium alone or a mixture of titanium and another metal selected from the group consisting of but not limited to arsenic, cobalt, chromium, copper, iron, germanium, hafnium, magnesium, manganese, molybdenum, niobium, nickel, antimony, tin, uranium, vanadium, yttrium, zinc, zirconium, lanthanum, an actinide a lanthanide and mixtures thereof.

In an aspect of the invention, B is silicon alone or a mixture of silicon and another metal selected from the group consisting of but not limited to aluminum, arsenic, bismuth, boron, beryllium, cobalt, chromium, copper, iron, gallium, germanium, indium, lead, magnesium, manganese, molybdenum, niobium, nickel, antimony, tin, titanium, vanadium, tungsten, zinc, and mixtures thereof.

The Na-ETS-10 zeolite may be structurally modified by any of the known techniques that are described in for example, U.S. Pat. Nos. 5,208,006 and 5,244,650, which are incorporated herein by reference. For example, the structurally modified molecular sieves may be prepared from a reaction mixture containing a source of titanium or titanium and at least one other metal capable of being octahedrally coordinated and also containing a source of silicon or silicon and at least one other metal capable of being tetrahedrally coordinated in the framework structure, a source of alkalinity such as an alkali or alkaline earth metal hydroxide, water and, optionally, an alkali or alkaline earth metal salt.

In an aspect of the invention, a structurally modified ETS-10 zeolite is prepared from a reaction mixture having a composition in terms of mole ratios of:
B/A=from about 1 to about 200
H$_2$O/B=from about 1 to about 100
M$_n$/A=from about 1 to about 100 wherein M indicates the cations of valence n derived from the alkali or earth metal and metal salts, and A and B are defined as above.

In an aspect of the invention, a structurally modified ETS-10 zeolite is prepared from a reaction mixture having a composition in terms of mole ratios of:
SiO$_2$/Al=from about 1 to about 200
SiO$_2$/Ti=from about 2 to about 20
H$_2$O/SiO$_2$=from about 2 to about 100
M$_n$/SiO$_2$=from about 0.1 to about 20
wherein M indicates the cations of valence n derived from the alkali or earth metal and metal salts. Such, aluminum modified ETS-10 zeolites have been dubbed, ETAS-10 zeolites (see U.S. Pat. No. 5,244,650).

The Na-ETS-10 may also be modified by adding a source of metal which is capable of being octahedrally or tetrahedrally coordinated within the titanosilicate framework structure, to a previously prepared Na-ETS-10. By way of non-limiting example, a source of aluminum (e.g. AlCl$_3$.6H$_2$O) may be added to previously prepared Na-ETS-10 to exchange silicon for aluminum, which is described in U.S. Pat. No. 5,244,650 (see especially Examples 1-7) that is incorporated herein by reference. The source of metal which is capable of being octahedrally or tetrahedrally coordinated in the framework structure may be stirred and heated with the as prepared Na-ETS-10 in the presence or absence of solvent or water to effect Ti and/or Si substitution. Other well known methods for mixing zeolites with additive compounds may also be used.

The current invention also contemplates modifications that remove (i.e. extract) a portion of the titanium from an "as prepared" Na-ETS-10, provided that the framework structure of the Na-ETS-10 remains intact and that the zeolite remains selective for olefin adsorption. Methods to remove titanium from an ETS-10 type zeolite are described in U.S. Pat. No. 5,906,954 and include treating the zeolite with complexing agents such as but not limited to ethylene diamine tetraacetic acid, oxalic acid and citric acid, amines, hydroxyl carboxylates and beta diketones.

In an aspect of the invention, the modified ETS-10 zeolite is an "as prepared" ETS-10 zeolite that has been both cationically modified and structurally modified.

The modified ETS-10 zeolites used in the current invention can be used in a wide variety of forms. For example, the modified ETS-10 zeolites may be in the form of a powder, a granule, an extrudate or other particulate form suitable for use in an adsorbent bed. The modified zeolites can be mixed with other components prior to use as an adsorbent most typically in an adsorbent bed. For example, natural or synthetic clays, aluminophosphates, agglomerates of clay and silica, silica or other metal oxides, and mixtures thereof may be added to the modified ETS-10 zeolties.

The modified ETS-10 zeolites can be used with any cycle swing adsorption process for the separation/enrichment of binary or multi-component mixtures of olefins and paraffins. For example, pressure swing adsorption (PSA) processes including vacuum swing adsorption (VSA), thermal swing adsorption (TSA) processes and combinations thereof can be used. The cycle swing adsorption process can comprise multiple adsorption and regeneration steps as well as purging and depressurization steps. Pressure swing and temperature swing processes are well known in the art.

Pressure swing adsorption can include, in addition to adsorption and regeneration steps: purge steps, venting steps, pressure equalization steps, evacuation steps, blowdown steps. Steps can be carried out in concurrent, alternating or sequential fashion and gas flows can be continuous, discontinuous, co-current and counter-current, all of which are well known in the art. In a PSA process one or more adsorbent beds can be arranged in series or in parallel. Some non-limiting examples of PSA processes are described in *Adsorption, Gas Separation* in the Kirk-Othmer Encyclopedia of Chemical Technology, Copyright John Wiley & Sons, Inc. vol 1, pgs 642-647 and references cited therein as well as in U.S. Pat. Nos. 3,430,418; 4,589,888; 6,293,999; 6,197,092 and 6,497,750 all of which are incorporated herein by reference.

Temperature swing adsorption (TSA) is described in Adsorption, Gas Separation in the Kirk-Othmer Encyclopedia of Chemical Technology, Copyright John Wiley & Sons, Inc. vol 1, pgs 636-642 and references cited therein all of which are incorporated herein by reference.

In an aspect of the present invention, at least one modified ETS-10 adsorbent bed is used in a pressure swing adsorption process to separate/enrich gaseous mixtures of olefins and paraffins having the same number of carbon atoms, preferably for the separation of ethylene from, or the enrichment of ethylene within, a gaseous mixture containing ethylene and ethane.

In an aspect of the present invention, at least one modified ETS-10 adsorbent bed is used in a pressure swing adsorption process carried out at ambient temperatures, to separate/enrich gaseous mixtures of olefins and paraffins having the same number of carbon atoms, preferably the separation of ethylene from, or the enrichment of ethylene within, a gaseous mixture containing ethylene and ethane.

In another aspect of the invention, at least one modified ETS-10 adsorbent bed is used in a combined pressure swing/temperature swing adsorption process to separate/enrich gaseous mixtures of olefins and paraffins having the same number of carbon atoms, preferably the separation of ethylene from, or the enrichment of ethylene within, a gaseous mixture containing ethylene and ethane.

The pressures at which adsorption and regeneration steps are carried out are not specifically defined, and depend on a number of factors such as but not limited to the temperature used, the type of cation used to modify the Na-ETS-10 zeolite, the type of structural modification of the Na-ETS-10 zeolite, and the nature of the olefin and paraffin to be separated/enriched. Typically, the range of absolute pressures used during the adsorption step can be from about 10 kPa to about 2,000 kPa, preferably from about 50 kPa to about 1000 kPa. The range of pressures used during the release of adsorbate (i.e. during the regeneration step) can be from about 0.01 kPa to about 150 kPa, preferably from about 0.1 kPa to about 50 kPa.

The temperatures at which the adsorption over the modified ETS-10 zeolite takes place will depend on a number of factors, such as but not limited to the particular olefin and paraffin to be separated/enriched, the type of cation used to modify the Na-ETS-10 zeolite, the type of structural modification of the Na-ETS-10 zeolite, and the pressure at which adsorption is to be carried out. In general, the adsorption step can be carried out at from ambient temperatures to above about 100° C., provided that the temperatures do not exceed temperatures at which chemical reaction of the olefin, such as a polymerization reaction, takes place. Temperatures that favor adsorption and desorption over the pressure range of about 0.1 kPa to about 1000 kPa are generally preferred. For reasons of economics, in one aspect of the current invention, it is desirable to use ambient temperatures during both the adsorption and desorption steps.

In an aspect of the current invention, a cationically modified ETS-10 zeolite has a superior pressure swing capacity for ethylene and ethane adsorption/desorption, in the pressure range of about 1 kPa to about 200 kPa, than an unmodified Na-ETS-10 zeolite.

In an aspect of the current invention, a cationically modified ETS-10 zeolite has a pressure swing capacity of at least about 0.5 mmol/g, preferably at least about 1.0 mmol/g for ethylene, in the pressure range of about 1 kPa to about 200 kPa, at a temperature of about 25° C.

In an aspect of the current invention, a modified ETS-10 zeolite is used to selectively adsorb ethylene from a gaseous feedstream containing ethylene and ethane, to produce an adsorbed phase enriched in ethylene and a non-adsorbed phase enriched in ethane. Desorption from the modified ETS-10 zeolite occurs at a pressure which is lower than the adsorption pressure, and a gaseous mixture rich in ethylene is recovered as product or may be further enriched by further treatment with modified ETS-10 zeolite. The feedstream may optionally contain gases such as carbon monoxide, carbon dioxide and hydrogen. However, it is preferable to treat the feedstream to remove carbon monoxide, carbon dioxide and hydrogen, prior to contact with the modified ETS-10 adsorbent. Components such as hydrogen sulfide may also be present in the feedstream and are preferably removed prior to contact with the adsorbent. Methods to remove hydrogen, hydrogen sulfide, carbon monoxide etc. are well known in the art.

In the current invention, the modified ETS-10 zeolite can be used in a pressure swing adsorption (PSA) process that receives product feedstreams from a hydrocarbons cracking unit or plant. A hydrocarbon cracking unit typically employs hydrothermal pyrolysis or high temperature catalytic processes to crack feedstocks such as but not limited to natural gas, naphtha and gas oil, for the production of light olefins such as ethylene and propylene. Preferred cracking processes include stream cracking of ethane to form ethylene, as used in a conventional ethane hydrocracking plant.

The methods and processes of the current invention can be used in a variety of petroleum refining and petrochemical operations where the separation of ethylene/ethane product streams is desired. For example, the current process can be used to perform a rough separation of ethylene and ethane prior to cryogenic fractionation of ethylene and ethane or alternatively to perform a final purification or finishing step after a rough cut distillative separation of ethylene and ethane. Cryogenic fractionation of ethylene from ethane is well known in the art. The generation of a C2 feedstream from the products of hydrocracking is also well known in the art and principally involves compression, acetylene hydrogenation, de-methanization, and various fractionation steps to remove higher olefins and higher paraffins.

In the present invention, modified ETS-10 zeolites can be used in one or more PSA beds, upstream of a ethylene/ethane distillation unit (i.e. a C2 splitter column). Alternatively, one or more PSA beds containing modified ETS-10 can be downstream of an ethylene/ethane distillation unit.

Without wishing to be bound by any single theory, use of PSA units containing modified ETS-10 zeolites can augment the separation performance of a C2 splitter column by increasing the proportion of olefins in a mixture of olefins and paraffin having the same number of carbon atoms. As a result, the investment and energy requirements for ethylene/ethane cryogenic separation, such as for example, the size of the C2 splitter column, may correspondingly be reduced.

EXAMPLES

Unmodified ("As Prepared") Na-ETS-10 Zeolites

Unmodified ETS-10 was synthesized hydrothermally as described in U.S. Pat. No. 5,011,591. A typical preparation involved thorough mixing of 50 g of sodium silicate (28.8% $SiO_2$, 9.14% $Na_2O$ obtained from Fisher Scientific), 2.3 g of sodium hydroxide (97+% NaOH, obtained from Fisher Scientific), 3.8 g of anhydrous KF (Fisher Scientific), 4 g of HCl (1M aqueous solution), and 16.3 g of $TiCl_3$ solution (30 wt. % Solution in 2N Hydrochloric Acid, from Fisher Scientific). The mixture was stirred in a blender for 1 h and then placed in a 125 mL sealed autoclave (by PARR Instruments) at 488 K for 64 h. This gave a resultant material that was washed with de-ionized water and dried in an oven at 373 K. The material could be extruded into a less than 100 mesh (<150 μm) powder.

Preparation of Modified ETS-10 Zeolites by Cation Exchange

Cation-exchange was carried out by exposing Na-ETS-10 material prepared as above (a less than 100 mesh powder) to an excess of aqueous ionic solution at 100° C. with stirring for 24 h. The aqueous ionic solutions added were alternatively an aqueous solution of LiCl, KCl, $BaCl_2$, $AgNO_3$ and $CuSO_4$. The exchanged materials were washed with de-ionized water and dried at 100° C.

Mixed cationic forms of ETS-10 including Ba/H and La/H forms were prepared by exposing Na-ETS-10 powder to 1 meq/g of an aqueous solution of $BaCl_2$ or $LaCl_3$ at 100° C. with stirring for 16 h. This provided partially exchanged materials that were then exposed to an HCl solution maintained at a pH of 2 for 8 h at 20° C. The final products were washed with de-ionized water and dried at 100° C.

Ethylene and Ethane Adsorption Studies

Ethylene and ethane adsorption isotherms were measured in a Rubotherm magnetic suspension balance (accuracy±μg), integrated into a GHP high pressure adsorption system constructed by VTI Corp. of Hialeah, Fla. Test samples were dried at 200° C. for 6 h under a vacuum of more than $10^{-4}$ Torr. Buoyancy effects were corrected with a helium displacement isotherm taken at the same temperature as the respective ethylene and ethane isotherms.

Nitrogen adsorption isotherms at −196° C. were measured in an AUTOSORB-1 volumetric system from Quantachrome Instruments, Boynton Beach Fla. Nitrogen isotherms for all the modified ETS-10 samples are type I according to the IUPAC classification (see Rouquerol et. al. in *Adsorption by Powders and Porous Solids: Principles, Methodology and Applications*. Academic Press, San Diego, Calif.). Equivalent specific surface ($S_{total}$) was calculated by applying the BET equation, and external surface ($S_{ext}$), internal surface ($S_{int}$) and micropore volume ($V_{mic}$) were calculated by the V-t method (see Greg, S. J; Sing, K. S. W. in Adsorption, Surface Area and Porosity. 1982 Academic Press, London-New York and Rouquerol, F. Rouquerol, J.; Sing, K. S. W. in Adsorption by Powders and Porous Solids: Principles, Methodology and Applications. Academic Press, San Diego Calif.). Surface analysis results are given in Table 1.

TABLE 1

Surface Analysis for Unmodified Na-ETS-10 and Modified ETS-10

| Adsorbent | $S_{total}$ (m²/g) | $S_{ext}$ (m²/g) | $S_{int}$ (m²/g) | $V_{mic}$ (cc/g) |
|---|---|---|---|---|
| Na-ETS-10 | 289 | 28 | 261 | 0.099 |
| K-ETS-10 | 178 | 28 | 150 | 0.067 |
| Li-ETS-10 | 321 | 22 | 299 | 0.123 |
| Ba-ETS-10 | 350 | 35 | 315 | 0.119 |
| Ba/H-ETS-10 | 417 | 30 | 387 | 0.146 |
| La/H-ETS-10 | 420 | 26 | 394 | 0.151 |
| Ag-ETS-10 | 209 | 19 | 190 | 0.071 |
| Cu-ETS-10 | 189 | 45 | 144 | 0.056 |

FIGS. 1*a*-1*h* shows the ethylene and ethane adsorption isotherms for unmodified Na-ETS-10 (FIG. 1*a*) and various cationically modified ETS-10 zeolites (FIGS. 1*b*-1*h*) at 25° C. A person skilled in the art will recognize that the isotherms for Na-ETS-10 and K-ETS-10 are rectangular in shape, consistent with a low pressure swing capacity. The isotherms for ETS-10 modified with Ag is very rectangular, indicative of irreversible adsorption and poor pressure swing capacity. In contrast, isotherms for ETS-10 modified with Li, Ba, Ba/H, La/H and Cu have greater curvature, consistent with an improved pressure swing capacity.

Modeling (Pure Component Isotherms and Binary Ethylene/Ethane Mixture)

Model analysis of ethylene and ethane adsorption isotherms for the modified and unmodified ETS-10 zeolites were carried out by following the procedure described by Al-Baghli and Loughlin in *J. Chem. Eng. Data* 2005, v 50, p 843 and *J. Chem. Eng. Data* 2006, v 51, p 248, which are incorporated herein by reference. Experimental isotherms for ethylene and ethane adsorption were fitted using the Tóth equation:

$$n = n_m \cdot p / (b+p)^{1/t},$$

where n is the amount of ethylene or ethane adsorbed (in mmol) at a pressure, p (in kilopascals, kPa), $n_m$ is the monolayer adsorption capacity of the adsorbent (in mmol/g), t can vary from 0 to 1, and b is related to the Henry's law constant, K by the expression:

$$K = n_m \cdot b^{-1/t}.$$

The selectivity, α of the adsorbent, in the Henry's law region is defined as the ratio of the Henry's law constants of the pure gas components:

$$\alpha = K_{ethylene} / K_{ethane}$$

In order to determine physically meaningful fitting values for monolayer adsorption capacity, $n_m$ and the selectivity, α the magnitude of $n_m$, was theoretically calculated, while the parameters b and t could vary during the fitting to the experimental data. To fit the equation, t and b were allowed to vary (with t varying from 0 to 1) until optimum parameters were obtained, using any well known fitting or regression technique, such as but not limited to the least squares technique, using the $n_m$ value determined as below. This "constrained regression" method for the Tóth equation fitting is described by Al-Baghli and Loughlin in *J. Chem. Eng. Data*, 2005, v 50, p 843 which is incorporated herein by reference.

The monolayer adsorption capacity is determined using the equation:

$$n_m = 0.95(\epsilon / V^*),$$

where ε is the monolayer volume of the adsorbent (in cc/g), V* is the molar volume (in cc/mol) of the adsorbate at the temperature of the isotherm measurement, and the factor 0.95 accounts for steric effects (see Al-Baghli and Loughlin in *J. Chem. Eng. Data,* 2005, v 50, p 843). The value for ε can be calculated directly from the nitrogen isotherm at −196° C. by applying the BET equation according to known methods. The value for ϵ can also be obtained form the surface parameters given in Table 1 using the equation:

$$\epsilon = (S_{total}/S_{int}) \cdot V_{mic},$$

where $S_{total}$, $S_{int}$ and $V_{mic}$ are defined as above. The molar volume, V* can be approximated by the Van der Waals volume, which is 0.055 cc/mol for ethylene and 0.063 cc/mol for ethane under supercritical conditions for the adsorbable gases.

The "constrained" Tóth equation fits well with most of the experimentally determined ethylene and ethane adsorption isotherms in the pressure range of from 1 to 200 kPa for the modified ETS-10 zeolites (see FIGS. 1a-1h). Some deviation between the model and the experimental data is observed in the case of Li-ETS-10.

Model predictions for binary ethylene/ethane adsorption isotherms were carried out by applying the ideal adsorption solution theory (IAST) developed by Myers and Prausnitz in *Thermodynamics of Mixed Gas Adsorption*, A.I.Ch.E. Journal, vol 11, No 1, pg 121 and as used by Al-Baghli and Loughlin in *J. Chem. Eng. Data* 2006, v 51, p 248, which are incorporated herein by reference. The algorithm proposed by Valenzuela and Myers in the *Adsorption Equilibrium Data Handbook*, 1989, Prentice Hall, Englewood Cliffs, N.J., which is incorporated herein by reference, was used to for the IAST mathematical analysis.

The "constrained" Tóth equation was used as a model to generate pure compound isotherms for the IAST calculations. The constrained Tóth parameters used for the IAST calculations are given in Tables B and C.

TABLE 2

Constrained Tóth Parameters for Adsorption of Ethylene at 25.5° C.

| Adsorbent | $n_m$ (mmol/g) | b (kPa$^t$) | t | K (mmol/g kPa) |
|---|---|---|---|---|
| Na-ETS-10 | 1.89 | 0.24 | 0.37 | 89.45 |
| K-ETS-10 | 1.37 | 0.42 | 0.59 | 5.96 |
| Li-ETS-10 | 2.28 | 0.51 | 0.50 | 8.77 |
| Ba-ETS-10 | 2.28 | 0.86 | 0.48 | 3.12 |
| Ba/H-ETS-10 | 2.72 | 2.12 | 0.53 | 0.66 |
| La/H-ETS-10 | 2.78 | 3.36 | 0.56 | 0.32 |
| Ag-ETS-10 | 1.35 | 0.29 | 0.33 | 57.47 |
| Cu-ETS-10 | 1.27 | 1.89 | 0.53 | 0.38 |

TABLE 3

Constrained Tóth Parameters for Adsorption of Ethane at 25.5° C.

| Adsorbent | $n_m$ (mmol/g) | b (kPa$^t$) | t | K (mmol/g kPa) |
|---|---|---|---|---|
| Na-ETS-10 | 1.65 | 0.54 | 0.40 | 7.70 |
| K-ETS-10 | 1.20 | 1.04 | 0.62 | 1.13 |
| Li-ETS-10 | 1.99 | 1.37 | 0.63 | 1.21 |
| Ba-ETS-10 | 1.99 | 1.71 | 0.58 | 0.79 |
| Ba/H-ETS-10 | 2.37 | 3.25 | 0.57 | 0.30 |
| La/H-ETS-10 | 2.43 | 3.36 | 0.55 | 0.27 |
| Ag-ETS-10 | 1.18 | 0.58 | 0.41 | 4.46 |
| Cu-ETS-10 | 1.11 | 2.01 | 0.47 | 0.25 |

The IAST selectivity, $\alpha_{ij}$ of the adsorbent, for the adsorption of ethylene from a mixture of ethylene and ethane was calculated at a given total pressure using the following equation:

$$\alpha_{ij} = y_i \cdot x_j / y_j \cdot x_i,$$

where, $x_i$, $y_i$ are the molar fractions of ethane in the adsorbed phase and the gas phase respectively, and $x_j$ and $y_j$ are the molar fractions of ethylene in the adsorbed phase and gas phase respectively.

Figure 1A:
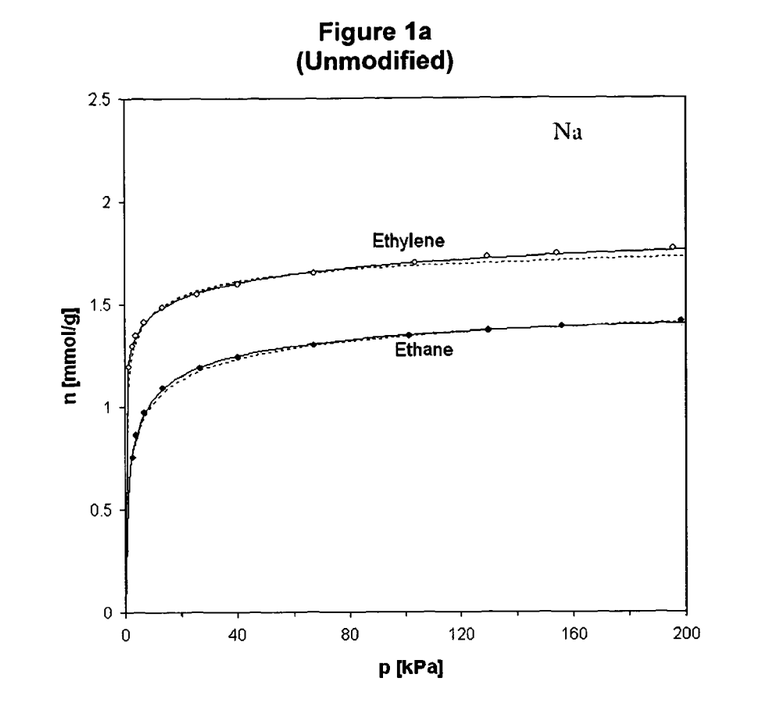
FIG. 1a, shows ethylene (open circles) and ethane (shaded circles) adsorption isotherms at 25° C. for an unmodified Na-ETS-10 zeolite. Dotted lines represent the constrained Tóth model isotherms.
Figure 1B:
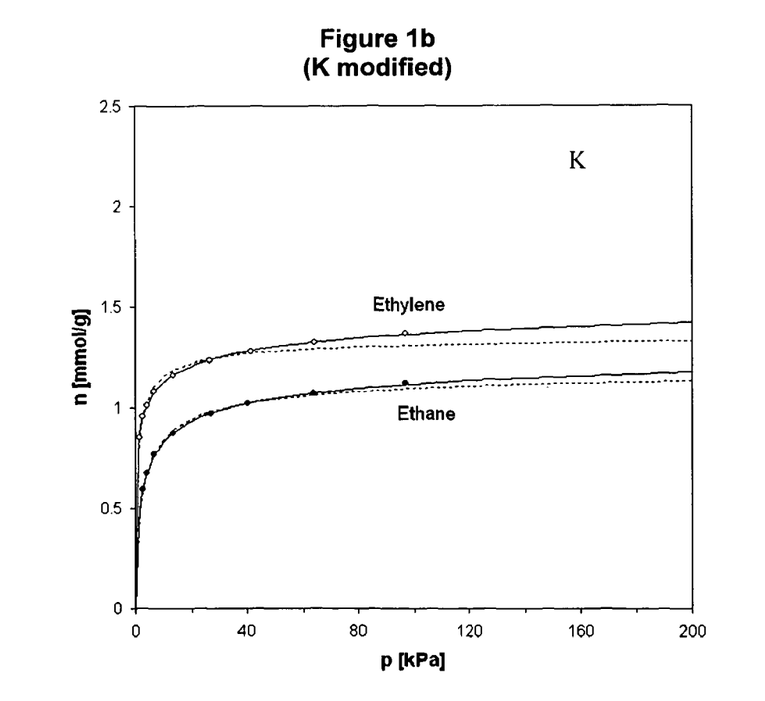
FIGS. 1b-1h, show ethylene (open circles) and ethane (shaded circles) adsorption isotherms at 25° C. for a series of cationically modified ETS-10 zeolites prepared according to the current invention. Dotted lines represent the constrained Tóth model isotherms.
Figure 1C:
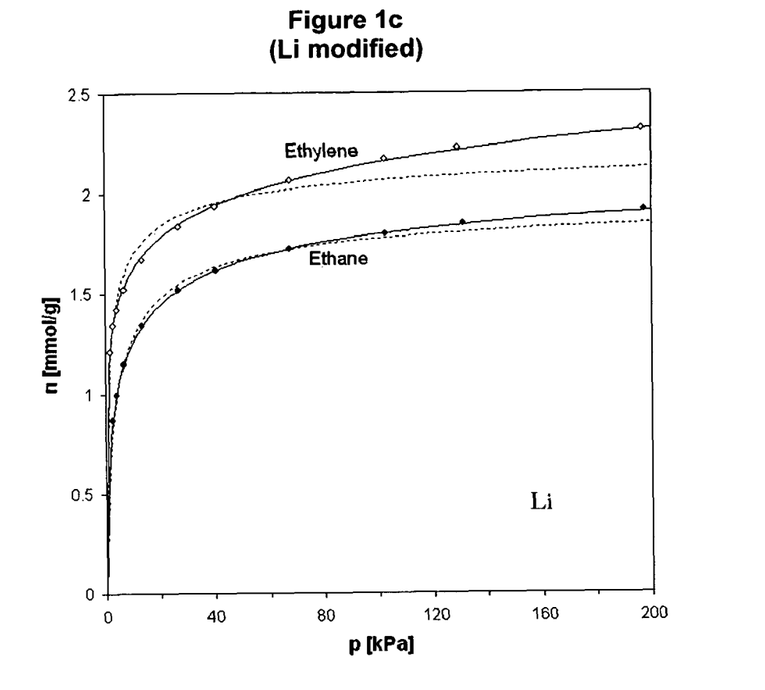
Figure 1D:
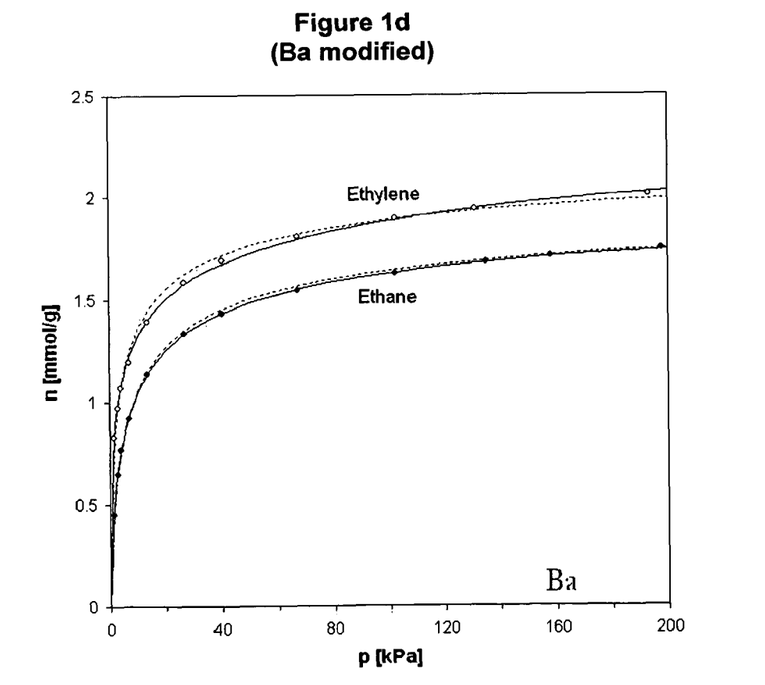
Figure 1E:
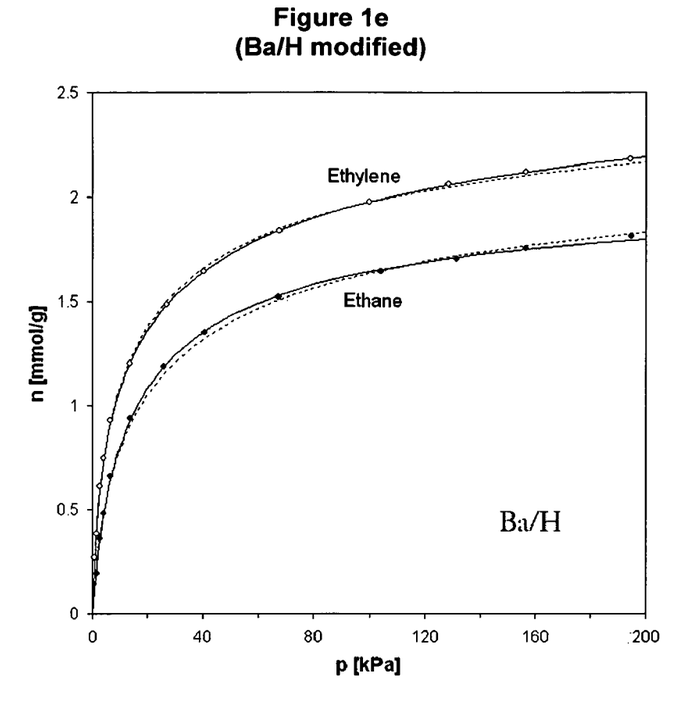
Figure 1F:
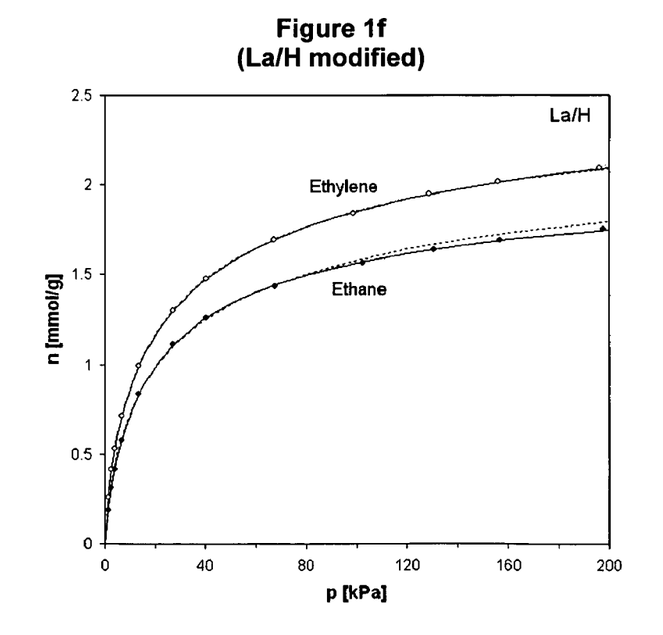
Figure 1G:
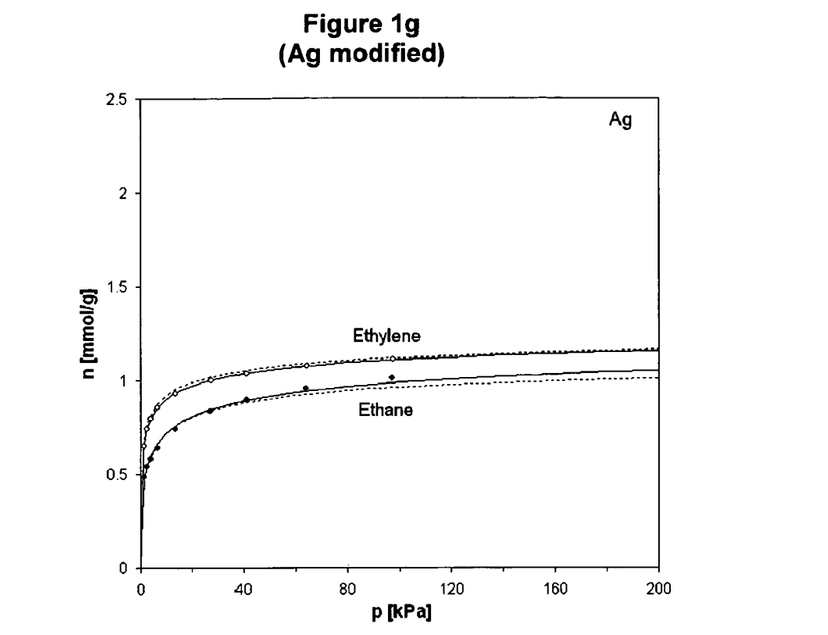
Figure 1H:
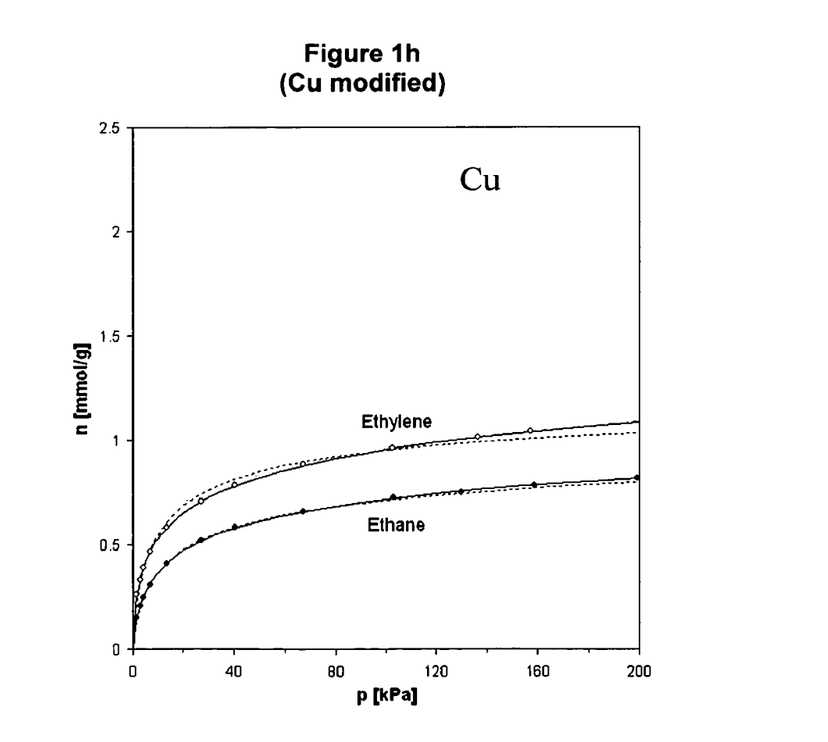
Figure 2A:
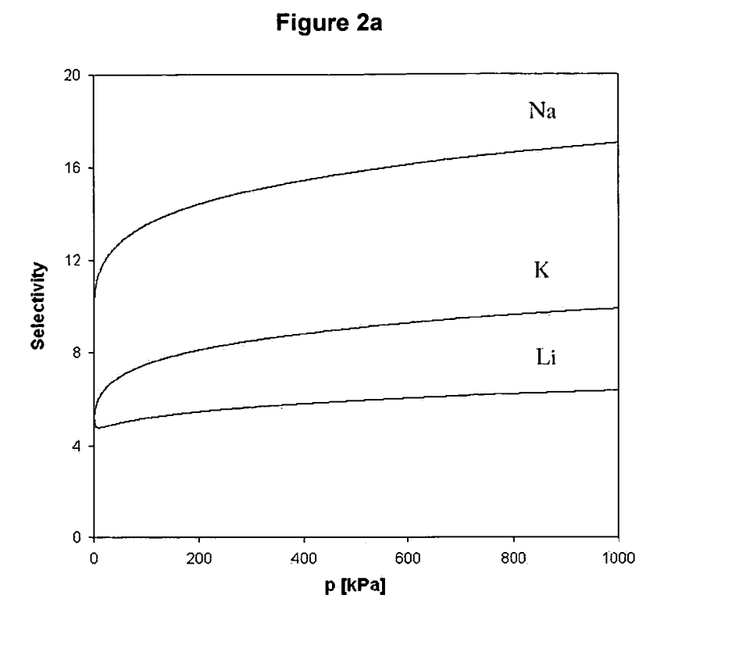
FIGS. 2a and 2b show the ideal adsorption solution theory (IAST) selectivity at 25° C. for a binary ethylene/ethane mixture (y=0.5) as a function of the total pressure for Na-ETS-10 and a series of cationically modified ETS-10 zeolites prepared according to the current invention.
Figure 2B:
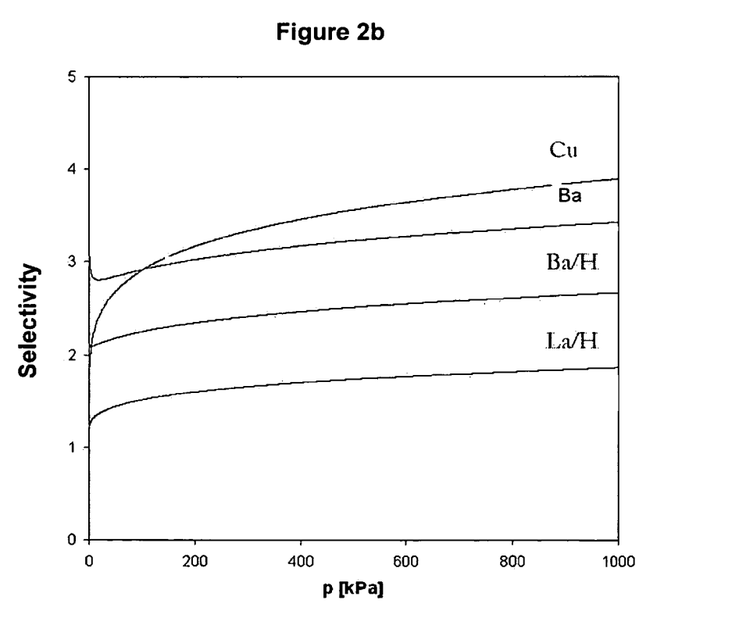

FIGS. 2a and 2b show the Ideal Adsorption Solution Theory (IAST) ethylene/ethane selectivity at 25° C., as a function of the total pressure, for unmodified and cationically modified ETS-10 zeolites (y is equal to 0.5). The IAST model shows that the ethylene/ethane selectivity generally increases with pressure. A person skilled in the art will recognize that modification with Li, Cu, Ba, BaH, and La/H leads to lower IAST selectivity than for unmodified Na-ETS-10 zeolites. However, comparison of FIGS. 1 and 2 shows that a good balance of IAST selectivity and pressure swing capacity can be obtained by suitable modification.

Figure 3:
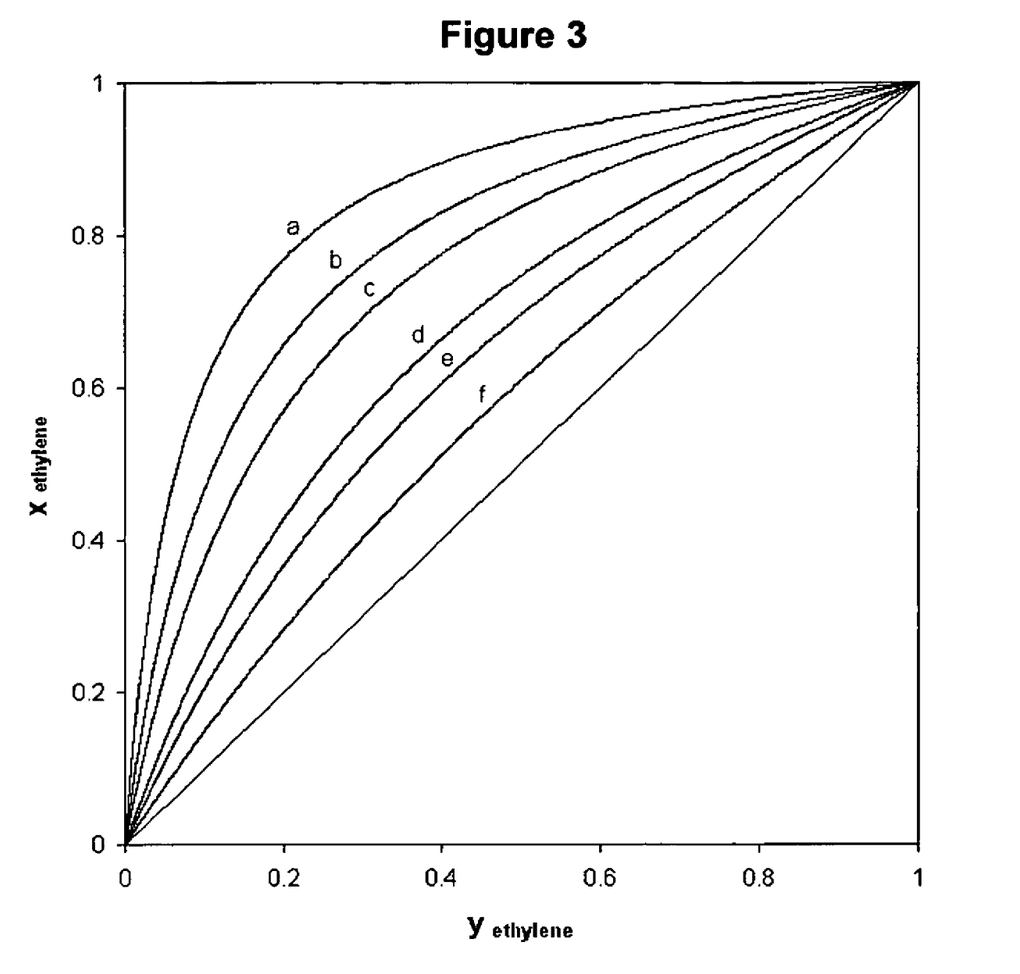
FIG. 3 shows the IAST plot of $y_{ethylene}$ vs. $x_{ethylene}$ at 25° C. and a total pressure of 150 kPa for unmodified (a) Na-ETS-10 and cationically modified, (b) K, (c) Li, (d) Cu and Ba (e) Ba/H and (f) La/H, ETS-10 zeolites prepared according to the current invention.

FIG. 3 shows the IAST plot of the molar fraction of ethylene in the gas phase ($Y_{ethylene}$) vs. the molar fraction of ethylene adsorbed ($X_{ethylene}$) for various modified ETS-10 zeolites, at 25° C. and a total pressure of 150 kPa; (a) as prepared Na-ETS-10; (b) K, (c) Li, (d) Cu and Ba (e) Ba/H and (f) La/H cation modified ETS-10 zeolites.

What is claimed is:

1. A method of increasing the proportion of olefin in a gaseous mixture comprising said olefin and a paraffin having the same number of carbon atoms as said olefin, wherein said process comprises:
    passing said mixture over a modified ETS-10 zeolite at a temperature and pressure wherein said modified ETS-10 material selectively adsorbs said olefin from said mixture, and
    lowering the pressure and optionally increasing the temperature to release the selectively adsorbed olefin from said modified ETS-10 zeolite.

2. The method of claim 1, wherein said olefin is ethylene and said paraffin is ethane.

3. The method of claim 2, wherein said modified ETS-10 zeolite comprises an as prepared Na-ETS-10 zeolite which has been modified by cation exchange with one or more than one mono-, di- or tri-valent cation or mixtures thereof.

4. The method of claim 3, wherein said as prepared Na-ETS-10 zeolite comprises pores having a size of about 8 Angstroms.

5. The method of claim 4, wherein said as prepared Na-ETS-10 zeolite has an oxide mole ratio which is represented by:

x M$_2$O:TiO$_2$:y SiO$_2$:z H$_2$O, wherein M is Na$^+$ or both Na$^+$ and K$^+$, x is from 1 to 10, y is from 2.5 to 25, and z is from 0 to 150.

6. The method of claim 5, wherein said modified ETS-10 zeolite comprises an as prepared Na-ETS-10 zeolite which has been modified with one or more than one mono-, di- or tri-valent metal cation, a proton or mixtures thereof.

7. The method of claim 6, wherein said metal cation is selected from the group consisting of Li$^+$, Cu$^+$, Ba$^{2+}$, Sr$^{2+}$, La$^{3+}$ and mixtures thereof.

8. The method of claim 6, wherein said modified ETS-10 zeolite comprises an as prepared Na-ETS-10 that has been modified with Ba$^{2+}$, or both Ba$^{2+}$ and H$^+$ or both La$^{3+}$ and H$^+$.

9. The method of claim 8, wherein the adsorption and release of ethylene is carried out at ambient temperature.

10. A method for the selective sequestration of ethylene from a gaseous mixture comprising ethylene and ethane, wherein said method comprises:
    passing said mixture over an adsorbent which selectively adsorbs ethylene from said mixture, said adsorbent comprising an as prepared Na-ETS-10 zeolite which has been modified by cation exchange with one or more than one mono-, di- or tri-valent cation or mixtures thereof.

11. A pressure swing adsorption process for increasing the proportion of an olefin in a gaseous mixture comprising said olefin and a paraffin having the same number of carbon atoms as said olefin, wherein said process comprises:
   passing said mixture through a bed comprising a modified ETS-10 zeolite at a pressure at which the bed selectively adsorbs said olefin to give a waste or recycle stream enriched in paraffin;
   reducing the pressure in said bed to a pressure at which the bed releases said adsorbed olefin to give a product stream enriched in olefin;
   wherein said modified ETS-10 zeolite comprises an as prepared Na-ETS-10 zeolite which has been modified by cation exchange with one or more than one mono-, di- or tri-valent cation or mixtures thereof.

12. The process of claim 11, wherein said olefin is ethylene and said paraffin is ethane.

13. The process of claim 12, wherein the process is carried out at ambient temperature.

14. A process for the selective removal of ethylene from a gaseous mixture comprising ethylene and ethane, said gaseous mixture being a product feedstream from an ethane hydrocracking unit, wherein said process comprises:
   passing said mixture over an adsorbent which selectively adsorbs ethylene from said mixture, said adsorbent comprising an as prepared Na-ETS-10 zeolite which has been modified by cation exchange with one or more than one mono-, di- or tri-valent cation or mixtures thereof.

15. A process for the separation of an olefin from a mixture comprising said olefin and a paraffin having the same number of carbon atoms as said olefin, wherein said mixture is subjected to both cryogenic distillation and pressure swing adsorption (PSA), said PSA comprising:
   passing said mixture through one or more PSA beds containing a modified ETS-10 zeolite which selectively adsorbs said olefin; and
   regenerating said one or more PSA beds to produce a product stream enriched in said olefin.

16. The process of claim 15, wherein said one or more PSA units increase the ethylene concentration in a C2 product stream immediately upstream or immediately downstream of a C2 splitter column; said C2 splitter column receiving the C2 product stream in a hydrocarbons cracking plant.

17. A method to adjust the adsorption selectivity and the pressure swing capacity of an as prepared Na-ETS-10 zeolite for use in a pressure swing adsorption (PSA) separation of ethylene and ethane, said method comprising:
   modifying said as prepared Na-ETS-10 zeolite by cation exchange with one or more than one mono-, di- or tri-valent cation or mixtures thereof.

18. The method of claim 1, wherein said modified ETS-10 zeolite comprises a structural variant of an as prepared Na-ETS-10 zeolite, wherein said structural variant comprises:
   a crystalline molecular sieve having a pore size of at least 8 Angstrom units and having a composition consisting of in terms of mole ratios of oxide as follows:

$a(1.0\pm0.25)M_{2/n}O:AO_\alpha:d\ BO_\beta:0\text{-}100\ H_2O$ wherein A is octahedrally coordinated titanium alone or a mixture of octahedrally coordinated titanium and another octahedrally coordinated metal selected from the group consisting of arsenic, cobalt, chromium, copper, iron, germanium, hafnium, magnesium, manganese, molybdenum, niobium, nickel, antimony, tin, uranium, vanadium, yttrium, zinc, zirconium, lanthanum, an actinide and a lanthanide and mixtures thereof; B is silicon alone or a mixture of silicon and another metal selected from the group consisting of aluminum, arsenic, bismuth, boron, beryllium, cobalt, chromium, copper, iron, gallium, germanium, indium, lead, magnesium, manganese, molybdenum, niobium, nickel, antimony, tin, titanium, vanadium, tungsten, zinc, and mixtures thereof; M is at least one cation of valence n; $\alpha$ is ½ the valence of A; $\beta$ is ½ the valence of B; d is 2-100; a is equal to ½ the charge provided by the total of A and B with the proviso that when A is solely titanium, B cannot be solely silicon and that when B is solely Si, A cannot be solely Ti.

* * * * *